(12) United States Patent
Lin et al.

(10) Patent No.: US 10,610,170 B2
(45) Date of Patent: Apr. 7, 2020

(54) PATIENT POSITION MONITORING SYSTEM BASED ON 3D SURFACE ACQUISITION TECHNIQUE

(71) Applicant: CARESTREAM HEALTH, INC., Rochester, NY (US)

(72) Inventors: Yuan Lin, Rochester, NY (US); William J. Sehnert, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 194 days.

(21) Appl. No.: 15/970,951

(22) Filed: May 4, 2018

(65) Prior Publication Data

US 2018/0325472 A1     Nov. 15, 2018

Related U.S. Application Data

(60) Provisional application No. 62/505,183, filed on May 12, 2017, provisional application No. 62/597,964, filed on Dec. 13, 2017.

(51) Int. Cl.
*A61B 6/00* (2006.01)
*A61B 5/00* (2006.01)
(Continued)

(52) U.S. Cl.
CPC .............. *A61B 6/04* (2013.01); *A61B 5/0077* (2013.01); *A61B 6/0457* (2013.01); *A61B 6/08* (2013.01);
(Continued)

(58) Field of Classification Search
CPC ....... A61B 5/0077; A61B 6/025; A61B 6/032; A61B 6/04; A61B 6/0457; A61B 6/08; A61B 6/4085; A61B 6/4405; A61B 6/4429; A61B 6/4441; A61B 6/461; A61B 6/487; A61B 6/50; A61B 6/5205; A61B 6/527; A61B 6/541; A61B 6/545
See application file for complete search history.

(56) References Cited

U.S. PATENT DOCUMENTS 6,958,815 B2 * 10/2005 Bevilacqua ............ G01N 21/49
356/445
9,717,467 B2     8/2017 Litzenberger et al.
(Continued)

FOREIGN PATENT DOCUMENTS

WO           2016/003957         1/2016

OTHER PUBLICATIONS

Minfei Qiang et al., "Measurement of three-dimensional morphological characteristics of the calcaneus using CT image post-processing," Journal of Foot and Ankle Research, 2014, 7:19, 9 pages.
(Continued)

*Primary Examiner* — Mark R Gaworecki

(57) ABSTRACT

A method acquires reflectance image content from patient anatomy that is within a volume of an imaging apparatus defined between a radiation source and a detector and generates a surface contour image from the acquired reflectance image content. The generated surface contour image is compared with surface contour image metrics stored for the imaging apparatus and a recommended adjustment to the position of the patient anatomy is reported according to the comparison.

17 Claims, 12 Drawing Sheets

(51) Int. Cl.
*A61B 6/04* (2006.01)
*A61B 6/08* (2006.01)
*A61B 6/02* (2006.01)
*A61B 6/03* (2006.01)

(52) U.S. Cl.
CPC .......... *A61B 6/4405* (2013.01); *A61B 6/4429* (2013.01); *A61B 6/4441* (2013.01); *A61B 6/50* (2013.01); *A61B 6/545* (2013.01); *A61B 6/025* (2013.01); *A61B 6/032* (2013.01); *A61B 6/4085* (2013.01); *A61B 6/461* (2013.01); *A61B 6/487* (2013.01); *A61B 6/5205* (2013.01); *A61B 6/527* (2013.01); *A61B 6/541* (2013.01)

(56) References Cited

U.S. PATENT DOCUMENTS

| | | | |
|---|---|---|---|
| 10,172,574 B2* | 1/2019 | Schafer | A61B 6/02 |
| 2002/0065461 A1* | 5/2002 | Cosman | A61B 6/5247 600/426 |
| 2006/0285641 A1* | 12/2006 | Scherch | A61B 5/064 378/65 |
| 2008/0095302 A1 | 4/2008 | Ruhrnschopf et al. | |
| 2017/0011546 A1* | 1/2017 | Zatonyi | G06T 15/503 |
| 2017/0224272 A1* | 8/2017 | Liu | A61B 5/0088 |

OTHER PUBLICATIONS

Yuan Lin and Ehsan Samei, "A fast poly-energetic iterative FBP algorithm," Physics in Medicine and Biology 59, 2014, pp. 1655-1678.

Yuan Lin and Ehsan Samei, "An efficient polyenergetic SART (pSART) reconstruction algorithm for quantitative myocardial CT perfusion," Medical Physics, 41(2), Feb. 2014, pp. 021911-1-021911-14.

F. Edward Boas and Dominik Fleischmann, "CT artifacts: Causes and reduction techniques," Imaging Med. (2012), 4(2), pp. 229-240.

* cited by examiner

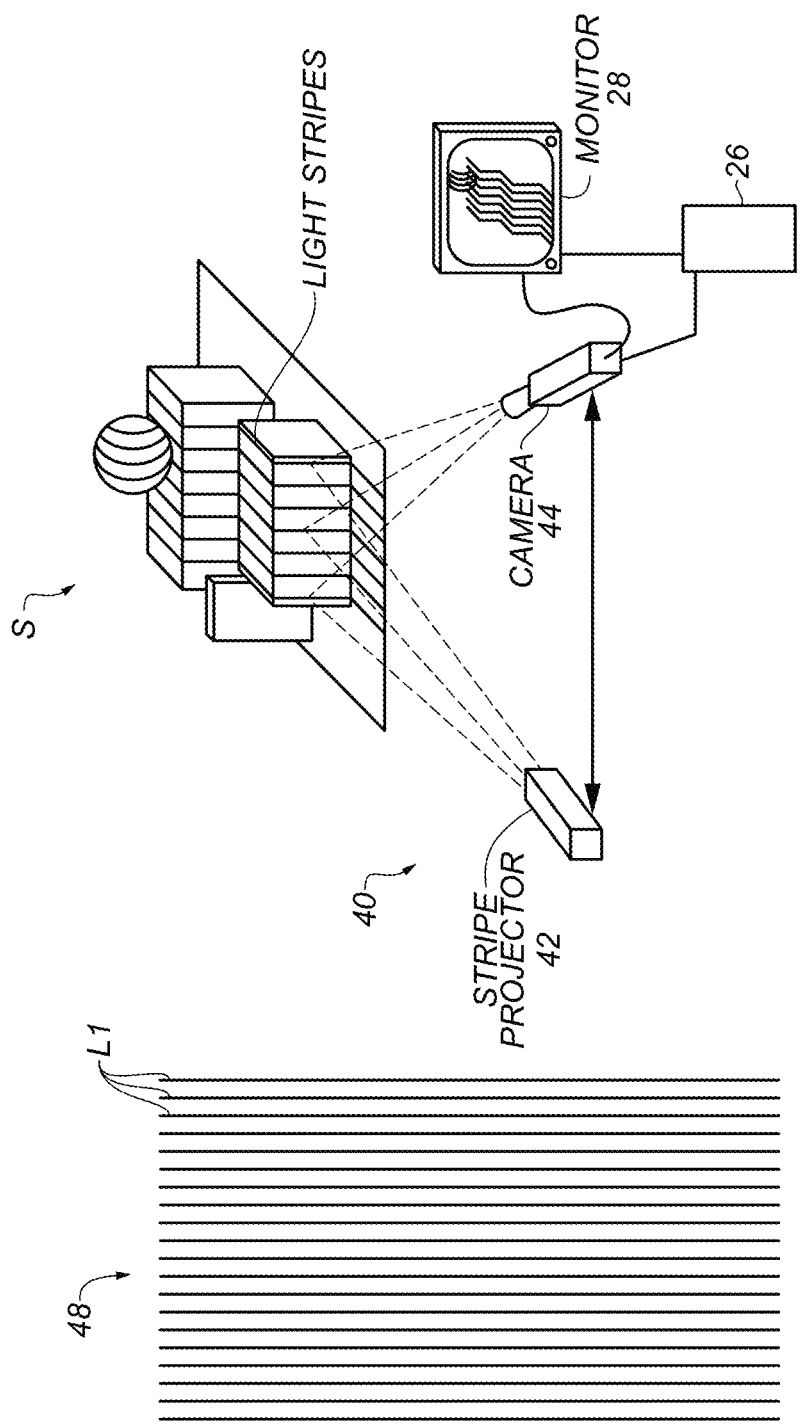

PATIENT POSITION MONITORING SYSTEM BASED ON 3D SURFACE ACQUISITION TECHNIQUE

CROSS REFERENCE TO RELATED APPLICATIONS

This application claims the benefit of U.S. Provisional Application Ser. No. 62/505,183, provisionally filed on May 12, 2017, entitled "PATIENT POSITION MONITORING SYSTEM BASED ON 3D SURFACE ACQUISITION TECHNIQUE", in the names of Yuan LIN and William J. SEHNERT, incorporated herein in its entirety.

This application claims the benefit of U.S. Provisional Application Ser. No. 62/597,964, provisionally filed on Dec. 13, 2017, entitled "PATIENT POSITION MONITORING SYSTEM BASED ON 3D SURFACE ACQUISITION TECHNIQUE", in the names of Yuan LIN and William J. SEHNERT, incorporated herein in its entirety.

TECHNICAL FIELD

The present disclosure relates generally to radiographic medical imaging and more particularly to imaging of patient anatomy wherein particular views of the anatomy are preferred and may be more familiar than others to the practitioner, and more likely to have diagnostic value for helping to guide patient assessment and treatment.

BACKGROUND

3-D volume imaging has proved to be a valuable diagnostic tool that offers significant advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Cone beam computed tomography (CBCT) or cone beam CT technology offers considerable promise as one type of diagnostic tool for providing 3-D volume images. Cone beam CT systems capture volumetric data sets by using a high frame-rate digital radiography (DR) detector and an x-ray source, typically affixed to a gantry that rotates about the object to be imaged, directing, from various points along its orbit around the subject, a divergent cone beam of x-rays toward the subject. The CBCT system captures projections throughout the rotation such as, for example, one 2-D projection image at every degree of rotation. The projections are then reconstructed into a 3D volume image using various techniques. Among well known methods for reconstructing the 3-D volume image from the 2-D image data are filtered back-projection approaches.

Although 3-D images of diagnostic quality can be generated using CBCT systems and technology, a number of technical challenges remain. The Applicants have recognized that one difficulty with obtaining suitable 3D volume images relates to patient pose. Inappropriate patient pose can cause various problems, for example:

(i) Inadvertent truncation of the anatomy. If the toes of a foot, for example, lie outside of the volume of interest (VOI), noticeable truncation artifacts can be induced and may significantly degrade the image quality and the Hounsfield Unit (HU) accuracy of the resulting images.

(ii) Poor alignment. If the body part being imaged is not well aligned with the reconstruction volume, the sagittal/coronal views that result can be tilted. This problem can make it difficult for the practitioner to analyze the images.

(iii) Inappropriate pose of the patient. When measuring three-dimensional morphological characteristics of the anatomy, the patient pose may not match a reference pose or standard pose that provides suitable information on the patient condition. If this is the case, the quantitative results (e.g., distance/angle between two bones) may not be readily comparable to established, reference values that facilitate proper assessment. Under some conditions with inappropriate positioning, patients might even need to undergo a repeated X-ray exam, causing additional X-ray dose to the patient.

Thus, it can be appreciated that methods to facilitate visualization of patient anatomy in standard poses can be of value for assisting practitioner assessment of patient condition and can help to reduce ambiguity in diagnosis.

SUMMARY

An object of the present disclosure is to address the difficulty of providing radiographic images of patient anatomy that have improved diagnostic value. Embodiments of the present disclosure are directed to apparatus and methods that help to automate and guide imaging personnel to acquire images in standard poses that facilitate diagnosis and treatment and help to improve efficiency of the imaging process, reducing or eliminating the need to obtain additional patient images with corresponding need for additional exposure.

Methods of the present invention can have particular value with imaging of patient extremities, such as arms, hands, legs, and feet, where results are best obtained with the subject anatomy imaged at particular pose positions.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided a method comprising: retrieving and displaying a stored image that shows predetermined positioning for an identified radiographic exam; acquiring reflectance image content for the identified radiographic exam from patient anatomy that is within a volume of an imaging apparatus defined between a radiation source and a detector; generating a surface contour image from the reflectance image content acquired from the patient anatomy; and displaying the generated surface contour image for comparison with the stored image that corresponds to the identified radiographic exam.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 5C shows operation of a surface contour imaging apparatus that applies the surface contour acquisition principles described with reference to FIGS. 5A and 5B.

DETAILED DESCRIPTION OF THE EMBODIMENTS

Figure 1:
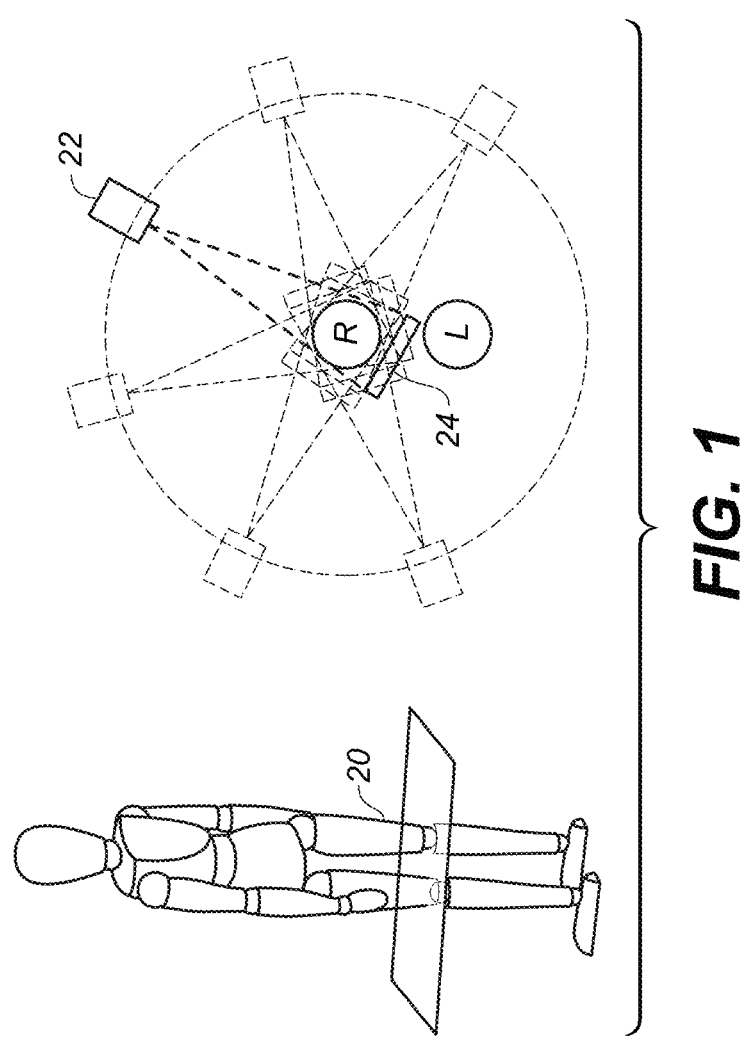
FIG. 1 is a schematic view showing the geometry and limitations of CBCT scanning for portions of the lower leg.

The following is a detailed description of the preferred embodiments, reference being made to the drawings in which the same reference numerals identify the same elements of structure in each of the several figures.

In the context of the present disclosure, the term "extremity" has its meaning as conventionally understood in diagnostic imaging parlance, referring to knees, legs, ankles, fingers, hands, wrists, elbows, arms, and shoulders and any other anatomical extremity. The term "subject" is used to describe the extremity or other anatomy of the patient that is imaged, such as the "subject leg", for example.

To describe the present invention in detail, a number of the examples given herein for embodiments of the present invention focus on imaging of the load-bearing lower extremities of the human anatomy, such as the leg, the knee, the ankle, and the foot, for example. Embodiments of the present disclosure can have particular advantages for acquiring volume images of patient anatomy using equipment that is particularly designed to provide suitable 2D or 3D volume images of extremities. However, these examples are considered to be illustrative and non-limiting. Embodiments of the present disclosure address the general problem of detecting and guiding overall patient pose and can be used with any number of radiographic imaging apparatus, for 2D or 3D volume imaging including, for example, not only extremity imaging apparatus but also chest x-ray imaging apparatus and various other types of radiographic imaging equipment.

In the context of the present disclosure, the term "arc" or, alternately, "circular arc", has its conventional meaning as being a portion of a circle of less than 360 degrees or, considered alternately, of less than $2\pi$ radians for a given radius.

The term "actuable" has its conventional meaning, relating to a device or component that is capable of effecting an action in response to a stimulus, such as in response to an electrical signal, for example.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, "volume image content" describes the reconstructed image data for an imaged subject, generally stored as a set of voxels. Image display utilities use the volume image content in order to display features within the volume, selecting specific voxels that represent the volume content for a particular slice or view of the imaged subject. Thus, volume image content is the body of resource information that is obtained from a CT, CBCT, MDCT, tomosynthesis, or other volume imaging reconstruction process and that can be used to generate depth visualizations of the imaged subject. The radiographic imaging apparatus defines a volume between the radiation source and the detector. For 3D imaging apparatus, the source and detector orbit the volume for anatomy imaging.

In extremity imaging, for example, there can be a limited range of possible angular rotation of the x-ray source and detector with respect to the subject. CBCT Imaging of legs, arms, and other extremities can be hampered by physical obstruction from a paired extremity. This is an obstacle that is encountered in obtaining CBCT image projections for the human leg or knee, for example. Not all imaging positions around the knee are accessible; the patient's own anatomy often prevents the radiation source and image detector from being positioned over a portion of the scan circumference.

To briefly illustrate a problem faced in CBCT imaging of the knee, the top view of FIG. 1 shows the circular scan paths for a radiation source 22 and detector 24 when imaging the right knee R of a patient as a subject 20. Various positions of radiation source 22 and detector 24 are shown in dashed line form. Source 22, placed at some distance from the knee, can be positioned at different points over an arc of about 200 degrees; with any larger arc the paired extremity, left knee L, blocks the way. Detector 24, smaller than source 22 and typically placed very near subject 20, can be positioned between the patient's right and left knees and is thus capable of positioning over the full circular orbit.

A full 360 degree orbit of the source and detector is not needed for conventional CBCT imaging; instead, sufficient information for image reconstruction can be obtained with an orbital scan range that just exceeds 180 degrees by the angle of the cone beam itself, for example. However, in some cases it can be difficult to obtain much more than about 180 degree revolution for imaging the knee or other joints and other applications. Moreover, there can be diagnostic situations in which obtaining projection images over a certain range of angles has advantages, but patient anatomy blocks the source, the detector, or both source and detector from imaging over that range.

Some of the proposed solutions for obtaining images of extremities under these conditions require the patient to assume a position that is awkward or uncomfortable. The position of the extremity, as imaged, may not be representative of how the limb or other extremity serves the patient in movement or under weight-bearing conditions. It can be helpful, for example, to examine the condition of a knee or ankle joint under the normal weight load exerted on that joint by the patient as well as in a relaxed, extended, or non weight-bearing position. But, if the patient is required to assume a position that is not usually encountered in typical movement or posture, there may be excessive strain or weight-bearing, or insufficient strain, or poorly directed strain or tension, on the joint. The knee or ankle joint, under some artificially applied load and at an angle not normally assumed when standing, may not behave exactly as it does when bearing the patient's weight in a standing position or in normal movement. Images of extremities under these conditions may fail to accurately represent how an extremity or joint behaves and is used, and may not provide sufficient information for assessment and treatment planning.

Still other difficulties with conventional solutions for extremity imaging relate to poor image quality. For image quality, the CBCT sequence requires that the detector be positioned close to the subject and that the source of the cone beam radiation be spaced apart at a sufficient distance from the subject. This arrangement provides the best image and reduces image truncation and consequent lost data. Positioning the subject midway between the detector and the source, as some conventional systems have done, not only noticeably compromises image quality, but also places the patient too near the radiation source, so that radiation levels are considerably higher. Concerns related to proper limb positioning can further compound this problem.

As is known to those skilled in the art, there are various; tomographic imaging modes that can be used to obtain depth information for a scanned extremity. Positioning for CBCT imaging represents a number of challenges that also affect other types of volume imaging, particularly modes that employ a radiation source and detector orbiting an extremity over a range of angles.

Figure 2:
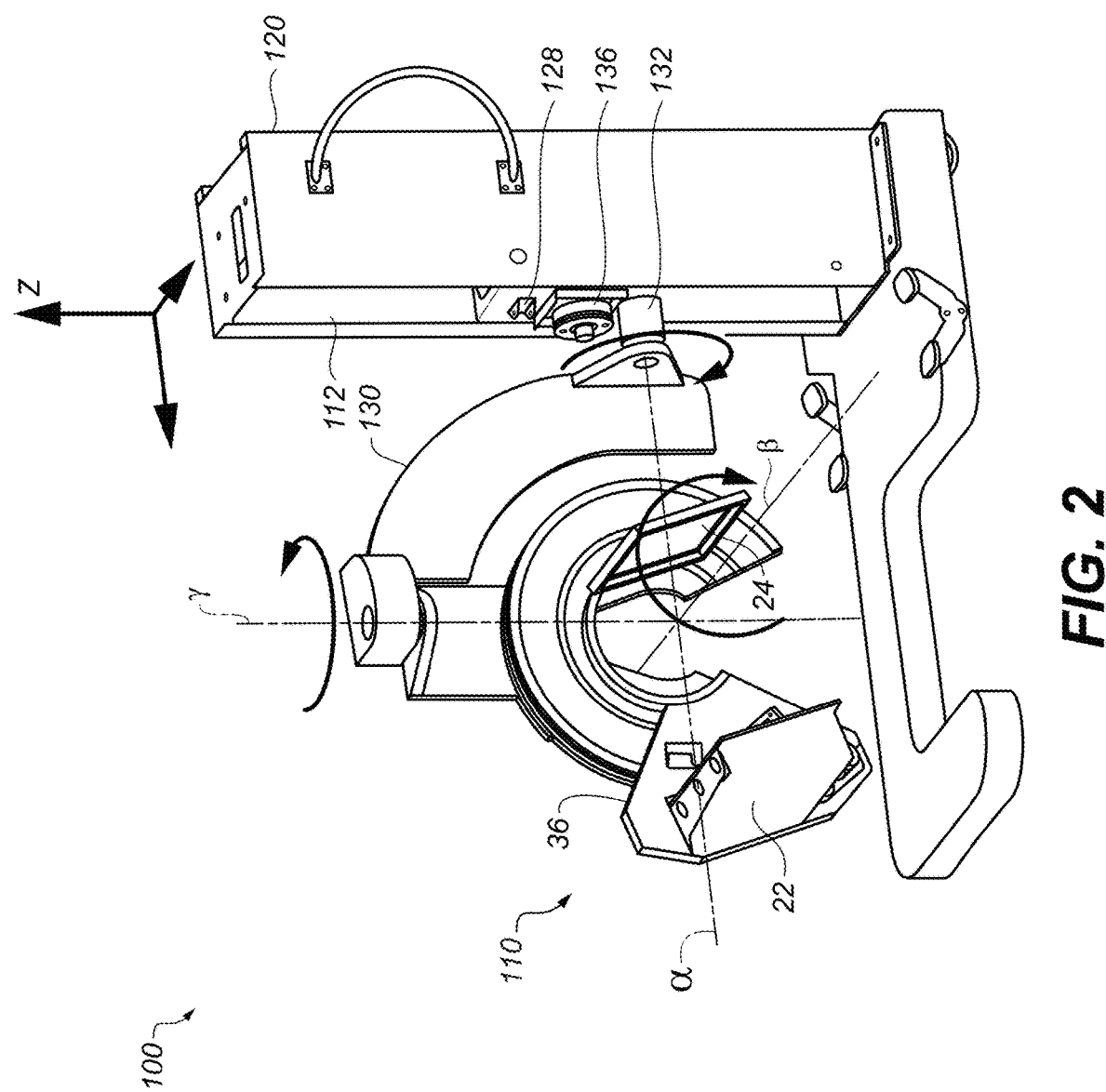
FIG. 2 is a perspective view of a CBCT imaging apparatus for extremity imaging.

Recently developed extremity imaging apparatus, such as that shown in perspective view in FIG. 2, have addressed the need for handling particular problems related to extremity imaging, including the following:

(i) improved placement of the radiation source and detector relative to the imaged subject to provide acceptable radiation levels and image quality throughout the scanning sequence, with the capability for at least coarse automated setup for examining an extremity under favorable conditions;

(ii) system flexibility for imaging at different heights with respect to the rotational axis of the source and detector, including the flexibility to allow imaging with the patient standing or seated comfortably, such as with a foot in an elevated position, for example;

(iii) capability to adjust the angle of the rotational axis to suit patient positioning requirements;

(iv) improved patient accessibility, so that the patient does not need to contort, twist, or unduly stress limbs or joints that may have been injured in order to provide images of those body parts;

(v) improved ergonomics for obtaining the CBCT image, allowing the patient to stand or sit with normal posture, for example. This would also allow load-bearing extremities, such as legs, knees, and ankles, to be imaged under the normal load exerted by the patient's weight, rather than under simulated loading conditions and provide options for supporting the patient; and (vi) adaptability for multi-use imaging, allowing a single imaging apparatus to be configurable for imaging any of a number of extremities, including knee, ankle, toe, hand, elbow, and other extremities. This also includes the capability to operate the imaging system in different imaging modes, including CBCT, two-dimensional (2D) projection radiography, fluoroscopy, and other tomography modes.

Extremity imaging apparatus 100 in FIG. 2 provides a configuration for comfortable positioning of the patient in a suitable posture for imaging. Imaging apparatus 100 allows the advantages of CBCT imaging to be adaptable for use with a range of extremities, to obtain volume images under a suitable imaging modality, with the image extremity presented at a suitable orientation under both load-bearing and non-load-bearing conditions, and with the patient appropriately standing or seated.

FIG. 2 shows portions of the internal imaging and positioning mechanisms (with covers removed) for a scanner 110 that allow imaging apparatus 100 the capability for imaging extremities with a variety of configurations. A complete description of imaging mechanics and features is provided, for example, in commonly assigned U.S. Pat. No. 9,717,467 to Litzenber et al., entitled "Extremity Imaging Apparatus for Cone Beam Computed Tomography", incorporated herein by reference in its entirety.

For a better understanding of the context of the present disclosure, it is useful to briefly review some aspects of the design and operation of imaging apparatus 100 as they relate to how extremity images can be acquired. Multiple axes allow the apparatus to provide scanning at various orientations, including horizontal scans, such as for legs and feet, and vertical scans, such as for arms, elbows, and hands. The α-axis and the γ-axis are non-parallel, to allow gimbaled action. According to an embodiment of the present invention as shown in FIG. 2, the α-axis and the γ-axis are mutually orthogonal. The α-axis is substantially orthogonal to the z-axis. The intersection of the α-axis and the γ-axis is offset from a support column 120 by some non-zero distance.

First considering the z-axis, FIG. 2 shows how vertical motion can be achieved. Within support column 120, a vertical carriage translation element 128 is actuated in order to travel upwards or downwards along column 120 within a track 112 in a vertical direction. Carriage translation element 128 has a support shaft 132 that is coupled to an actuator 136 for providing α-axis rotation to forked or C-shaped support arm 130. Forked support arm 130, shown only partially in FIG. 2 to allow a better view of underlying components, is coupled to support shaft 132. X-ray source 22 and detector 24 are mounted on a rotatable gantry 36 for rotation about a scan or central axis, designated as the β axis. Axis β is orthogonal to the α-axis and the γ-axis in the embodiment shown.

It can be appreciated that z-axis translation can be effected in a number of ways. Challenges addressed by the type of system that is used include handling the weight of forked support arm 130 and the imaging scanner 110 that arm 130 supports. This can easily weigh a few hundred pounds. In addition, precautions are provided for handling conditions such as power loss, contact with the patient, or mechanical problems that hamper positioning movement or operation.

Other features of support column 120 for vertical translation include built-in redundancy, with springs to absorb weight and impact, the load cell to sense a mechanical problem including obstruction by the patient, and manually operable brake mechanisms.

In order to help standardize X-ray imaging exams and to obtain consistent appearance of images for patients undergoing specific types of exams, the Applicants have developed a methodology for monitoring patient position and guiding the patient to attain a desired pose position prior to exposure. This method can help to alleviate various alignment related problems (e.g., truncation problems, difficulties related to tilted sagittal views, etc.) and patient pose related problems (e.g., foot not positioned on a flat surface, etc.)

In order to sense and guide patient position, embodiments of the present disclosure operate by acquiring a real-time 3D surface model of the patient anatomy within a volume of interest (VOI), with the surface model acquired using a 3D surface acquisition device. Predetermined positioning guidelines are stored and compared against the acquired anatomy position within the VOI. These guidelines establish parameters for acceptable body part positioning within the VOI and can detect and report on patient position, to help guide the patient and technician for suitable posing and to help avoid pose positions that will not provide acceptable results. Guidelines can be stored in the form of contour images with or without accompanying metrics.

This methodology can help with single-exposure imaging as well as with volume imaging, intuitively guiding the patient prior to and during exposure, such as for multiple X-ray acquisition (e.g., PA view and lateral view of hand, or palm opened view and palm closed view, etc.).

Various features of this methodology and associated apparatus are described herein. Among features and benefits of this method are the following:

(i) The 3D surface acquisition system can provide a real-time 3D surface model of the body part, which is shown on a display screen as reference information for the patient and attending technician;

(ii) The practitioner can define new patient poses for future use by saving the current 3D surface model in a database;

(iii) When scanning a patient, the acquired 3D surface model can be compared with the body part models in a database to differentiate the body part within the VOI;

(iv) The acquired 3D surface model can be used to verify that the correct body part is within the VOI and will be the anatomy that is exposed;

(v) The 3D surface model can be used to recommend body-part specific acquisition protocols;

(vi) The real-time 3D surface model can be further rendered with simulated anatomical structure to verify that the correct anatomical structure will be scanned;

(vii) The acquired 3D surface model can be used to ascertain that the body part is centered within the volume of interest and will not induce truncation problems;

(viii) The 3D surface model can be used to verify that the body part is oriented correctly, or used to compute volume rotation parameters, so that the final reconstructed volume can correctly display axial, sagittal, and coronal views;

(ix) The patient monitoring system can guide the patient to adapt a particular pose that is beneficial to diagnosis. For extremity CBCT imaging, practitioners may intend patients to adapt and maintain specific pose positions during the image acquisition process, because these positions can:

(a) assist in practitioner diagnosis of an underlying joint problem. For example, a weight-bearing position is generally preferred for lower extremity imaging; or (b) assist the practitioner to obtain meaningful and comparable measurement results from the scanned anatomical structure. For example, when measuring the three-dimensional morphological characteristics of the calcaneus, it can be preferred that the patient foot be positioned on a flat surface, rather than on a tilted surface.

(x) By specifying the body part and pose information, the practitioner can readily order desired multiple pose images of the same patient (e.g., either radiographic images or volume images of palm-opened pose and palm-closed pose positions) to examine how specific joints move in transition from one pose to another. The patient monitoring system can intuitively and sequentially guide the patient through multiple acquisitions based on a doctor's prescription.

(xi) The 3D model can also be used for acquisition protocol planning (e.g., tube current modulation), patient-specific dose estimation, motion correction, scatter estimation, and the like.

Obtaining accurate dimensional and angular data from bone structures and position also has diagnostic value. In some cases, dimensional and angular data can be readily measured with the subject anatomy in a standard. spatial orientation. Reference is hereby made to an article by Minfei Qiang, Yanxi Chen, Kin Zhang, Haobo Li, and Hao Dai entitled "Measurement of three-dimensional morphological characteristics of the calcaneus using CT image post-processing" in *Journal of Foot and Ankle Research.* 2014; 7:19 doi10.1186/1757-1146-7-19.

As previously indicated, embodiments of the present disclosure can have particular value for CBCT extremity imaging. An exemplary system of this type is shown in the schematic top views of FIG. 3 that show progressive stages in the operational sequence for obtaining CBCT projections of a portion of a patient's lower leg at a number of angular positions when using a CBCT imaging apparatus. The relative positions of radiation source 22 and detector 24, which may be concealed for protection under a hood or chassis, are shown at different representative acquisition angles in FIG. 3. In addition, a surface contour imaging apparatus 40 is provided, shown coupled to the radiation source 22 in this embodiment, and translated along the path followed by source 22, shown at a radial distance R2 from a center of orbit at axis f3, indicated with a cross in each schematic figure. Detector 24 follows a path at a radial distance R1 from the center. According to an embodiment of the present disclosure, surface contour imaging apparatus 40 includes a projection apparatus that is energizable to direct structured light toward the subject foot or leg that is the object to be imaged within the VOI and a camera that is disposed to acquire images of the structured light incident on the leg.

Figure 3:
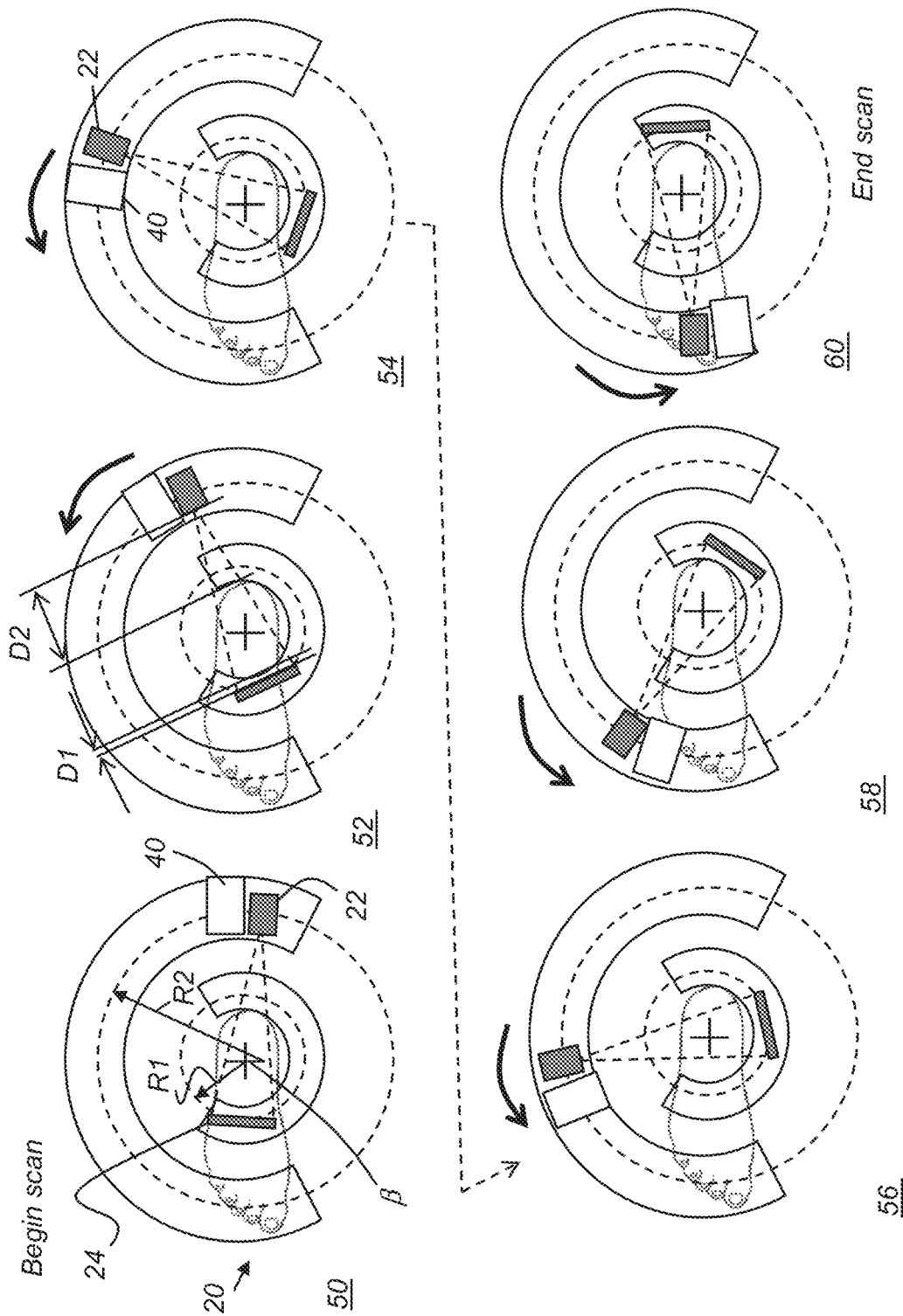
FIG. 3 shows portions of the operational sequence for obtaining CBCT projections of a portion of a patient's leg at a number of angular positions when using the imaging apparatus according to an embodiment of the present invention.

Still referring to FIG. 3, the source 22 and detector 24 are diametrically opposite each other at each position during the CBCT scan and projection imaging. The sequence begins at a begin scan position 50, with radiation source 22 and detector 24 at initial positions to obtain an image at a first angle. Then, both radiation source 22 and detector 24 orbit about axis β as represented in interim scan positions 52, 54, 56, and 58. Imaging terminates at an end scan position 60. As this sequence shows, source 22 and detector 24 are in diametrically opposing positions relative to subject 20 at each imaging angle. Throughout the scanning cycle, detector 24 is within a short distance D1 of subject 20. Source 22 is positioned beyond a longer distance D2 of subject 20. The positioning of source 22 and detector 24 components on each path can be carried out by separate actuators, one for each transport path, or by a single rotatable member. The actuator that moves source 22 can also move surface contour imaging apparatus 40 along the path. It should be noted that scanning motion in the opposite direction, that is, clockwise with respect to the example shown in FIG. 3, is also possible, with the corresponding changes in initial and terminal scan positions.

According to an embodiment of the present disclosure, an initial scan of the subject extremity executes, with only the surface contour imaging apparatus 40 energized and acquiring images for generating a 3D contour image of the leg. Exposure radiation is de-energized for this initial scan. During or immediately following this scan that uses reflectance imaging only, a computer or other control logic processor that is associated with the imaging apparatus generates contour image content that shows the position of the subject lower leg. The generated contour image content is then compared against stored information related to pose and position in order to determine whether or not the patient's leg is properly placed for subsequent CBCT exposure. For example, the leg may not be centered along axis β, as would generally be required for acquiring the needed image content for reconstruction. If the leg is properly positioned, the scan and exposure sequence for CBCT can be executed. If the leg is out of position, corrective instructions can be provided to the technician or patient for adjusting leg position. This initial reflectance-only image scan can be repeated as many times as needed until proper pose is verified. According to an embodiment of the present disclosure, there is no patient exposure until the leg position is determined to be correct.

Figure 4:
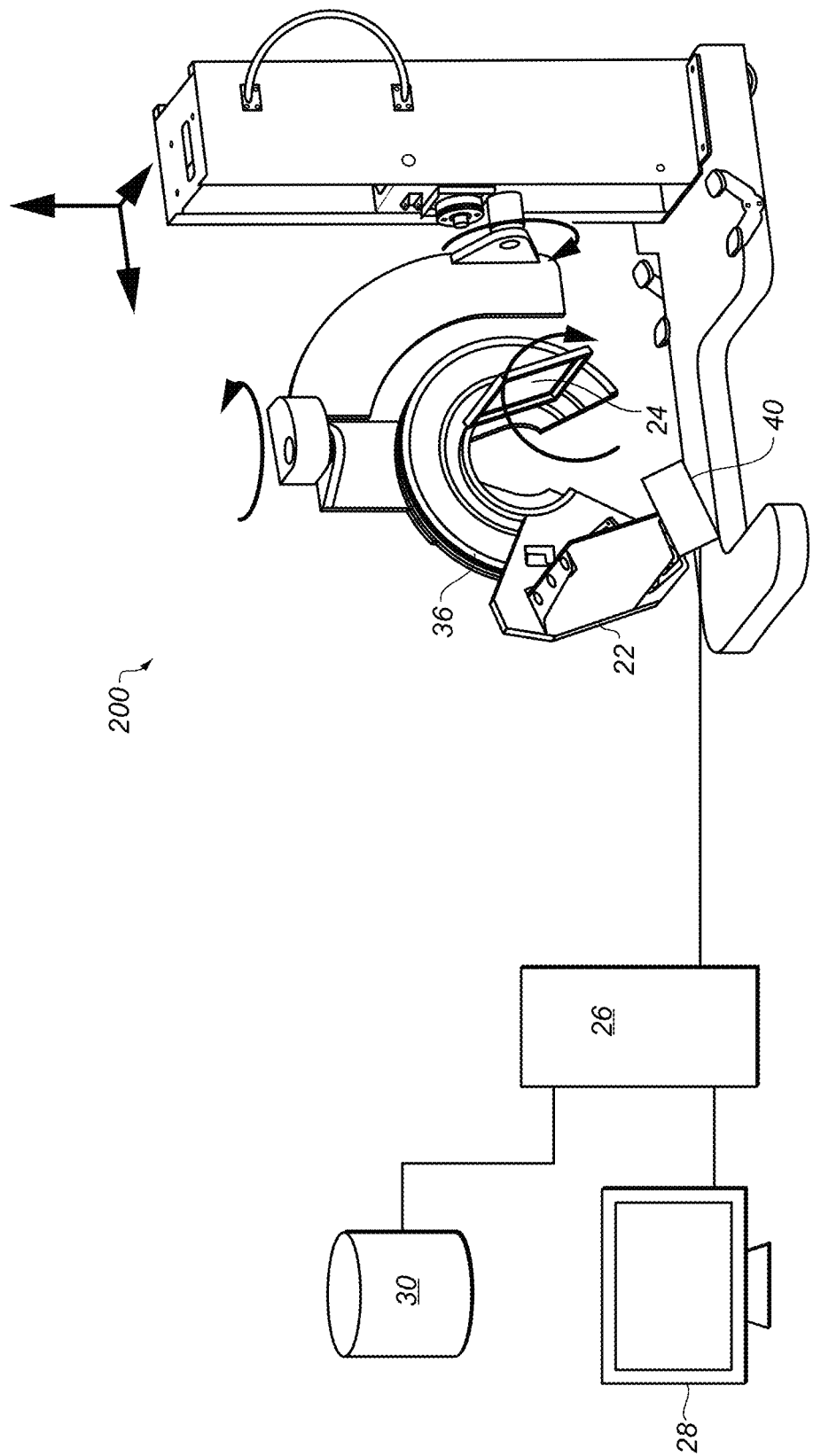
FIG. 4 is a schematic diagram that shows an imaging apparatus for acquiring both 3D surface contour imaging content and 3D volume imaging content.

The schematic diagram of FIG. 4 shows an imaging apparatus 200 for acquiring both 3D surface contour imaging content and 3D volume imaging content. Surface contour imaging apparatus 40 is shown coupled along gantry 36, such as to the transport mechanics that orbit source 22 about the VOI. A computer or other type of control logic processor 26 is in signal communication with surface contour imaging apparatus 40 for acquiring the reflectance image content and generating surface contour information. A display 28 is in signal communication with control logic processor 26 for reporting results and providing patient guidance for re-positioning if needed. A memory 30 in signal communication with control logic processor 26 stores information related to predetermined pose positioning for one or more exam types, used for comparison with the generated surface contour information.

It is noted that surface contour imaging apparatus 40 can be implemented in any of a number of ways consistent with methods of the present disclosure. FIG. 3 showed one possible arrangement, with surface contour imaging apparatus 40 coupled to source 22 and traveling along the same path used for source 22 orbit about the subject. In an alternate embodiment, surface contour imaging apparatus 40 is stationary, mounted alongside the travel path for CBCT imaging components. Multiple projectors and cameras can be used, mounted at different points along the component travel path.

Use With Other Radiography Apparatus

The system has been described for use with reference to patient positioning within a VOI for a CBCT apparatus. However, patient position sensing and verification can be useful for any of a number of types of radiographic imaging. Methods and apparatus of the present disclosure can be used to support 2D radiography imaging, for example, wherein the patient is positioned against a Bucky or other component that supports the x-ray detector. Proper positioning of the patient within the VOI can be important for various types of 2D x-ray exams. Support can also be provided for various types of 3D imaging apparatus as well, helping to accurately detect patient position and provide some type of feedback information for re-positioning the patient within the VDI prior to exposure.

Surface Contour Imaging

Figure 5A:
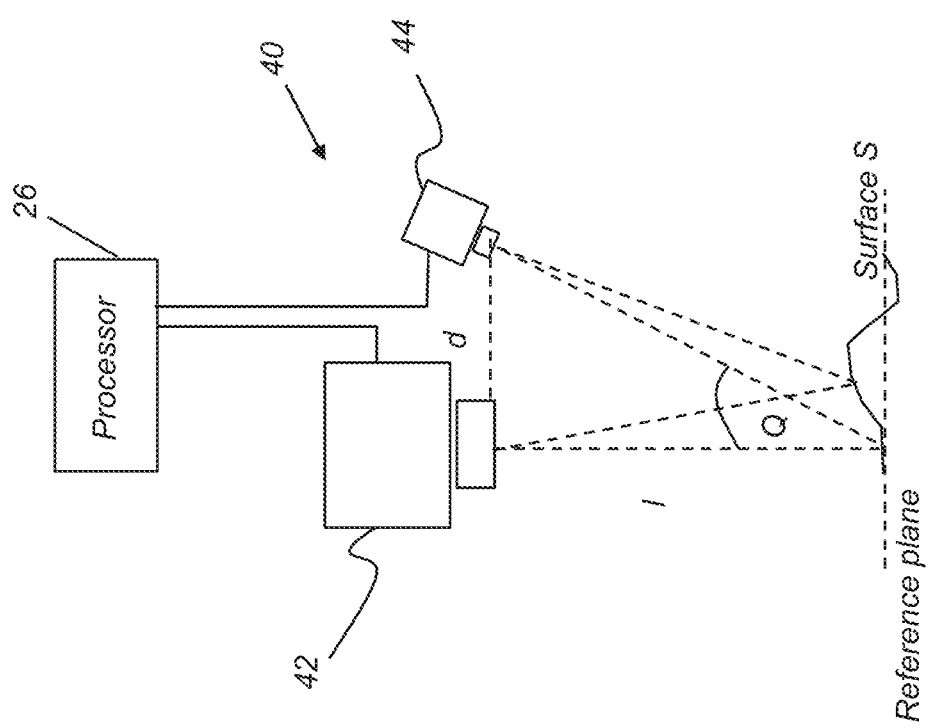
FIGS. 5A and 5B are schematic diagrams that show basic principles of surface contour imaging using structured light and triangularization.
Figure 5B:
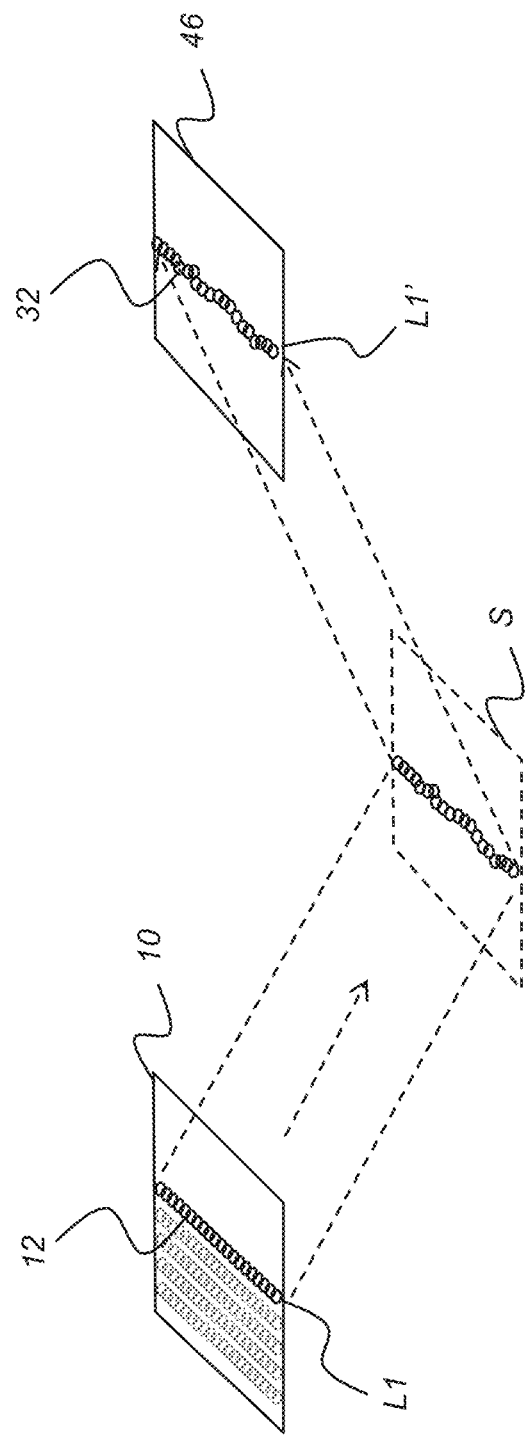

Structured light imaging is one well known type of reflectance surface contour imaging that can be employed by surface contour imaging apparatus 40. The schematic diagrams of FIGS. 5A and 5B show basic principles of surface contour imaging using structured light and triangularization. Provided within surface contour imaging apparatus 40, a projector 42 directs successive lines or other illumination pattern over a distance 1 onto the surface S at a reference plane. A camera 44, at the image plane and at a known distance d from projector 42, acquires image content corresponding to each projected line. Principal axes of projector 42 and camera 44 are offset from each other by an angle Q. Control logic processor 26 synchronizes operation of projector 42 and camera 44 and obtains, stores, and processes or transmits the acquired image data from camera 44 in order to characterize the surface contour of object O.

The schematic diagram of FIG. 5B shows, for the example of a single line of light L1 that is projected from an illumination array 10, how patterned light is used for obtaining surface contour information when using a conventional array source. A mapping is obtained as illumination array 10 directs a pattern of light from projector 42 onto a surface S and a corresponding image of a line L1' is formed on an imaging sensor array 46 of camera 44. Each pixel 32 on imaging sensor array 46 maps to a corresponding pixel 12 on illumination array 10 according to modulation by surface S. Shifts in pixel position, as represented in FIG. 5B, yield useful information about the contour of surface S. It can be appreciated that the basic pattern shown in FIG. 5B can be implemented in a number of ways, using a variety of illumination sources and sequences and using one or more different types of sensor arrays 46. Illumination array 10 can utilize any of a number of types of arrays used for light modulation, such as a liquid crystal array or digital micromirror array, such as that provided using the DLP (Digital Light Processor) micromirror array device from Texas Instruments Inc., Dallas, Tex.

Using the concept described with reference to FIG. 5B, conventional structured light imaging apparatus used for contour imaging, such as apparatus using digital light processor (DLP) and similar modulation systems, form and project a 2-D image, multiple lines at a time, onto the target surface.

The schematic diagram of FIG. 5C shows operation of surface contour imaging apparatus 40 that applies the surface contour acquisition principles described with reference to FIGS. 5A and 5B. Surface contour acquisition can be provided using projector 42 that generates and directs a pattern 48 of lines L1 or other features individually from a laser source or other reflectance light source at different orbital angles toward a surface S, represented in FIG. 5C by multiple geometric shapes. The combined line images of light reflected from the surface, recorded by camera 44 or other type of image sensor, from different angles but registered to geometric coordinates of the imaging system, provide structured light pattern information. Triangulation principles, as shown previously in FIG. 5A, are employed in order to interpret the detected projected light pattern and compute contour information to characterize patient anatomy or other surface using the detected line deviation, Lines L1, or other projected pattern, can be visible light or light of infrared wavelengths not visible to the patient and to the viewer, but visible to the appropriate imaging sensors.

Display 28 shows the acquired surface contour as reconstructed by control logic processor 26 using one or more surface contour reconstruction algorithms.

By projecting and capturing images that show structured light patterns that duplicate the illumination arrangement shown in FIG. 5B multiple times, as shown in the structured pattern 48 of FIG. 5C, the projected image provides information that simultaneously locates a number of surface points of the imaged object. This speeds the process of gathering many sample points, while the plane of light (and usually also the receiving camera) can be laterally moved in order to "paint" some or all of the exterior surface of the object with the plane of light. Multiple structured light patterns can be projected and analyzed together for a number of reasons, including to increase the density of lines for additional reconstructed points and to detect and/or correct incompatible line sequences. Incremental shifting of the line pattern and other techniques can help to compensate for inaccuracies and confusion that can result from abrupt transitions along the surface.

Among its beneficial features, structured light imaging can use reflected light of visible or near-visible wavelengths, harmless to the patient. This use of reflectance imaging allows structured light image content to be continuously generated before and during exposure, or generated as needed, before, during, or following exposure, allowing accurate monitoring of patient position for an exam.

In the context of the present disclosure, the phrase "3D surface imaging" refers broadly to any of a number of techniques that are used to obtain 3D surface, contour, and depth information for characterizing the surface features of a subject in the VOI. "Range imaging" is one class of 3D surface imaging that uses reflectance image content acquired from 2D image sensors. There are a number of types of 3D surface imaging approaches, each using information from a sequence of 2D reflectance images. 3D surface imaging techniques for acquiring 3D surface images familiar to those skilled in the imaging arts and suitable for use in various embodiments of the present disclosure include the following:

(i) Contour imaging using structured light illumination, as described with reference to FIGS. 5A-5C.

(ii) Depth from focus imaging. Also termed "structure from focus", methods applying this technique sweep the object plane using an optical scanner moving toward or away from the subject along a depth direction. This moving element allows the acquisition of a stack of 2D images, each acquired image corresponding to an observation at a specific depth (like a microscope). Each path of light from the scanner intersects the images from the volumes at various depths. An algorithm processes the acquired image data and determines a best depth value by analyzing local blur information, related to spatial frequencies. This gives a set of 3D points in focus which is representative of features on the observed surface.

(iii) Structure from motion. Algorithms that use structure from motion (SFM) provide a type of range imaging that allows depth estimation to be obtained from a sequence of 2D images from a camera that is moving about a 3D structure. Edge features and other salient features are tracked from image to image and used to characterize the surface contour as well as camera motion.

(iv) Active/passive stereophotogrammetry or single camera photogrammetry (also called SLAM (Simultaneous Localization And Mapping): Similar to SFM, two images of the same object are taken under slightly different observation orientations (either using two cameras at fixed relative spatial position or a single camera moved between two positions). Similar features (or landmarks) are paired between those two images. The set of corresponding landmarks is used to estimate the observation orientations (the relative camera orientation if not already known) and also determine a set of 3D points.

(v) Ultrasound. Ultrasound electronics can directly record a reflected signal returned from a transducer which is converted to depth information. An array of sources or a spatial or an angular sweeping technique may be used to collect depth information from the subject in the VOI along different paths. The echo from each path locates a 3D surface point. The combination of numerous 3D surface points defines a 3D surface contour.

(vi) Time of flight (TOF). TOF methods measure the propagating time of reflected light to extract depth information from an object. One type of TOF uses a pulse signal and a synchronized camera to record the flight time. The depth can be calculated using constant light speed. Another type of TOF uses a modulating wave and a synchronized camera, to record the phase shifting. The depth can be estimated from the shifted phase and the light speed.

(vii) Structure from shading (SFS). Methods using the SFS approach reconstruct the 3D shape of a surface from a single image in which pixel intensity along a surface relates to the angle between the illumination source for the surface and the surface normal at that pixel.

As noted in the above listing, the reflectance signal can be from reflected light of visible or near-visible ranges, at monochrome wavelength or broadband wavelength ranges. Reflected ultrasound signals can alternately be used for providing reflectance image content that indicates anatomy position.

The reflectance image content that is acquired can be used to generate a 3D point cloud or mesh, using techniques familiar to those skilled in the 3D reconstruction arts.

Operational Sequence

Figure 6:
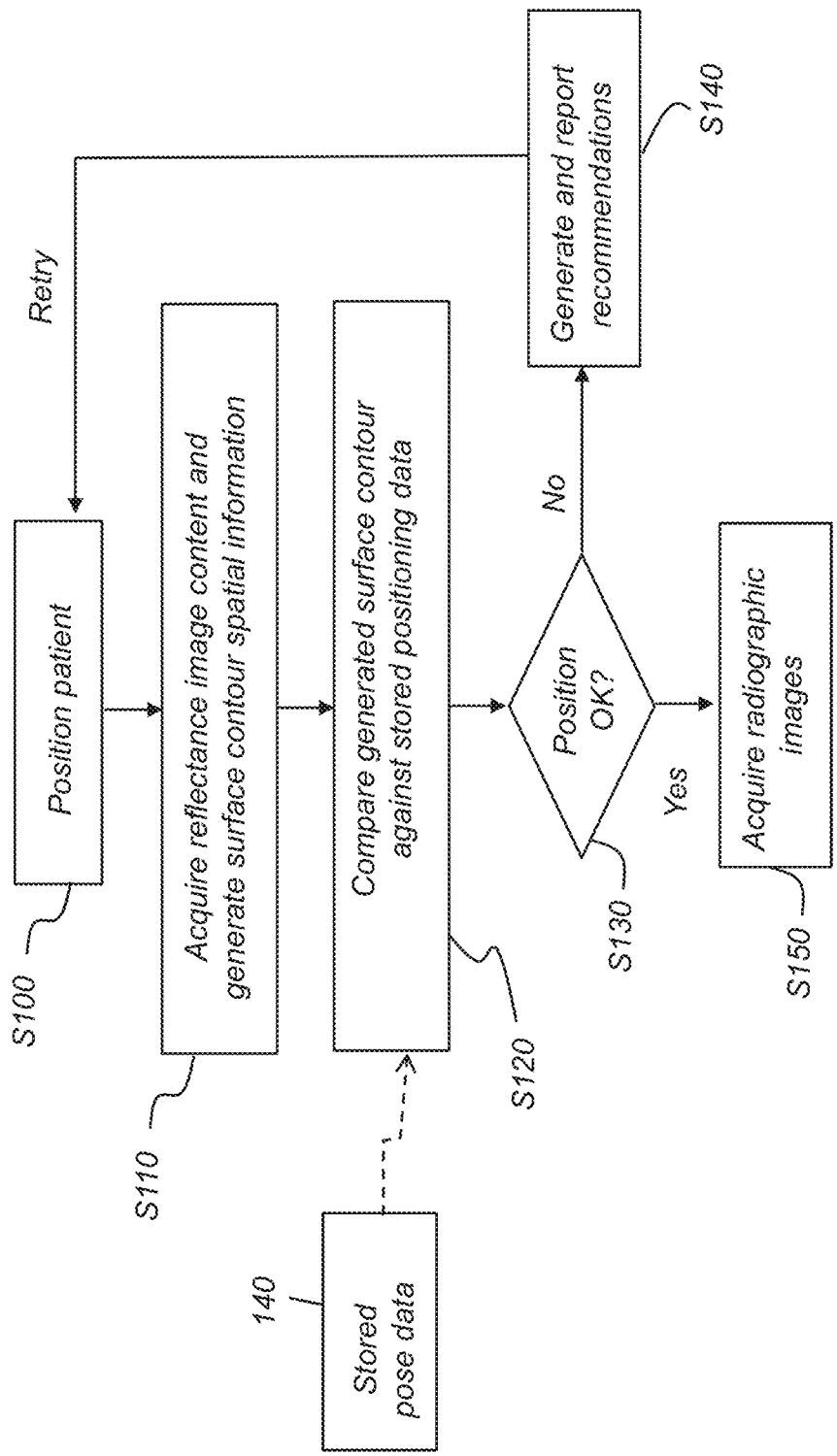
FIG. 6 is a logic flow diagram showing a sequence for patient positioning and verification according to an embodiment of the present disclosure.

FIG. 6 is a logic flow diagram showing an exemplary sequence for patient positioning and verification according to an embodiment of the present disclosure. In a positioning step S100, the patient is positioned or re-positioned within the VOI. In a surface contour characterization step S110, reflectance images of patient anatomy within the VOI such as the structured light images described previously with reference to FIGS. 5A-5C, are obtained and processed. The output of step S110 processing is surface contour information that can then be compared against predetermined pose data 140 stored by the imaging apparatus in. A comparison step S120 executes, comparing the output of step S110 against the stored pose data 140. The pose data 140 can be in the form of 3D data, such as an idealized contour shape within the imaging volume, or can be any of a number of metrics, such as distance from one or more reference points of the imaging apparatus, relative angle of surface features of the anatomy to the imaging apparatus or to other surface features, or other data.

Continuing with FIG. 6, a decision step S130 executes to determine whether or not the patient pose is within acceptable range to allow subsequent radiographic imaging in an acquisition step S150. If the patient pose deviates excessively from the desired stored pose data 140 for a particular exam, a report generation step S140 executes. Step S140 provides the feedback needed to alert the patient and imaging staff that repositioning is recommended. Report generation step S140 can provide displayed information, as described by example subsequently. Alternately, step S140 can provide audible feedback, such as a beeping sound, voice message, or a sound signal that varies depending on the level of the detected difference between intended and actual positions. Following patient response to step S140, the process can return to step S100 to recheck patient position.

Pose data 140 as noted in FIG. 6 can be stored from previous exams, indexed by various metrics, such as patient age, sex, height, weight, exam type, and other data. A library of standardized and customized poses can be generated and stored for use with particular types of imaging apparatus, such as provided by the manufacturer or integrator of the imaging system. In addition, a practitioner may have preferred or specialized poses that are developed and stored on a system or systems at a particular site. A sequence of instructions can be provided to a key operator for storing any number of patient poses, indexed for use by exam or patient factors. There can also be utility in storing pose data for a patient so that subsequent exams allow ready comparison over time, such as to show a healing or degenerative process.

According to an embodiment of the present disclosure, patient exposure is prevented by the radiographic imaging apparatus until proper positioning is detected. This preventive action can be subject to an override instruction entered by a technician or practitioner.

According to an alternate embodiment of the present disclosure, the predetermined, preferred surface contour or outline for an identified exam can simply be retrieved from data storage and displayed to the technician, along with a surface contour display showing the actual, current patient position. With this arrangement, the display can be provided only to serve as a guide for technician reference, without providing measurements or recommendations for corrective action. The operator can then visually approximate the preferred pose, comparing ideal and actual positioning to judge whether or not patient position is suitable based on experience, need for precision, and other factors.

Reporting Sensed Position

Figure 7A:
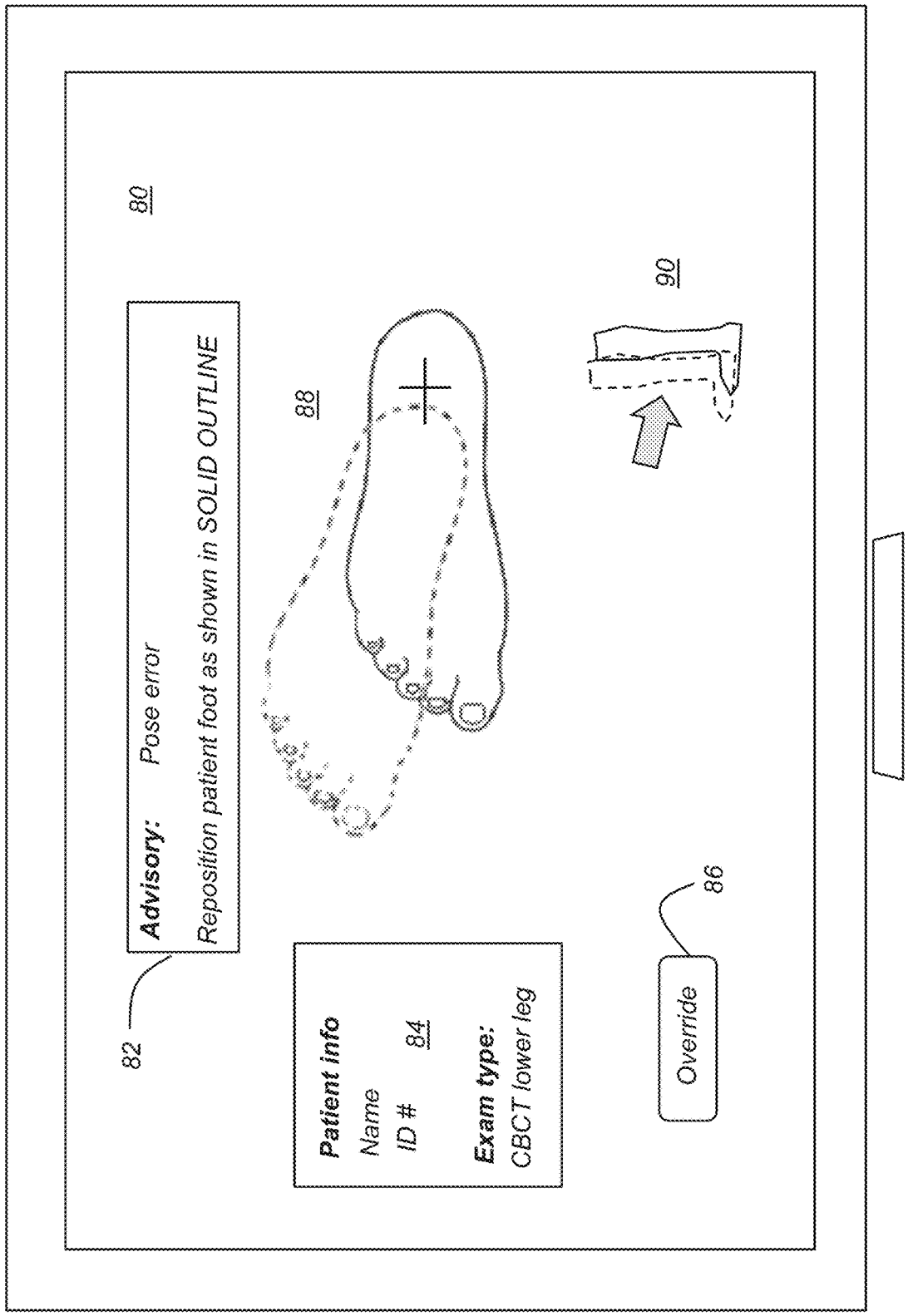
FIGS. 7A and 7B are schematic views that show exemplary report screens for reporting on the detected pose from surface contour information.

The schematic view of FIG. 7A shows an exemplary report screen 80 for reporting on the detected pose from surface contour information generated by control logic processor 26 (FIG. 4) as a result of report generation step S140 described with reference to FIG. 6. An advisory message 82 indicates the pose error type and recommended response. An exam information window 84 shows appropriate information about the patient and exam type. An override button 86 allows operator or practitioner override of the pose error results, allowing imaging under special circumstances. A top view 88 shows actual outline, such as in dashed form, for anatomy positioning and the desired outline. A side view 90 can show repositioning information in similar fashion. An instructional arrow or other indicator or animated sequence can be provided to help guide the patient or technician for repositioning.

Figure 7B:
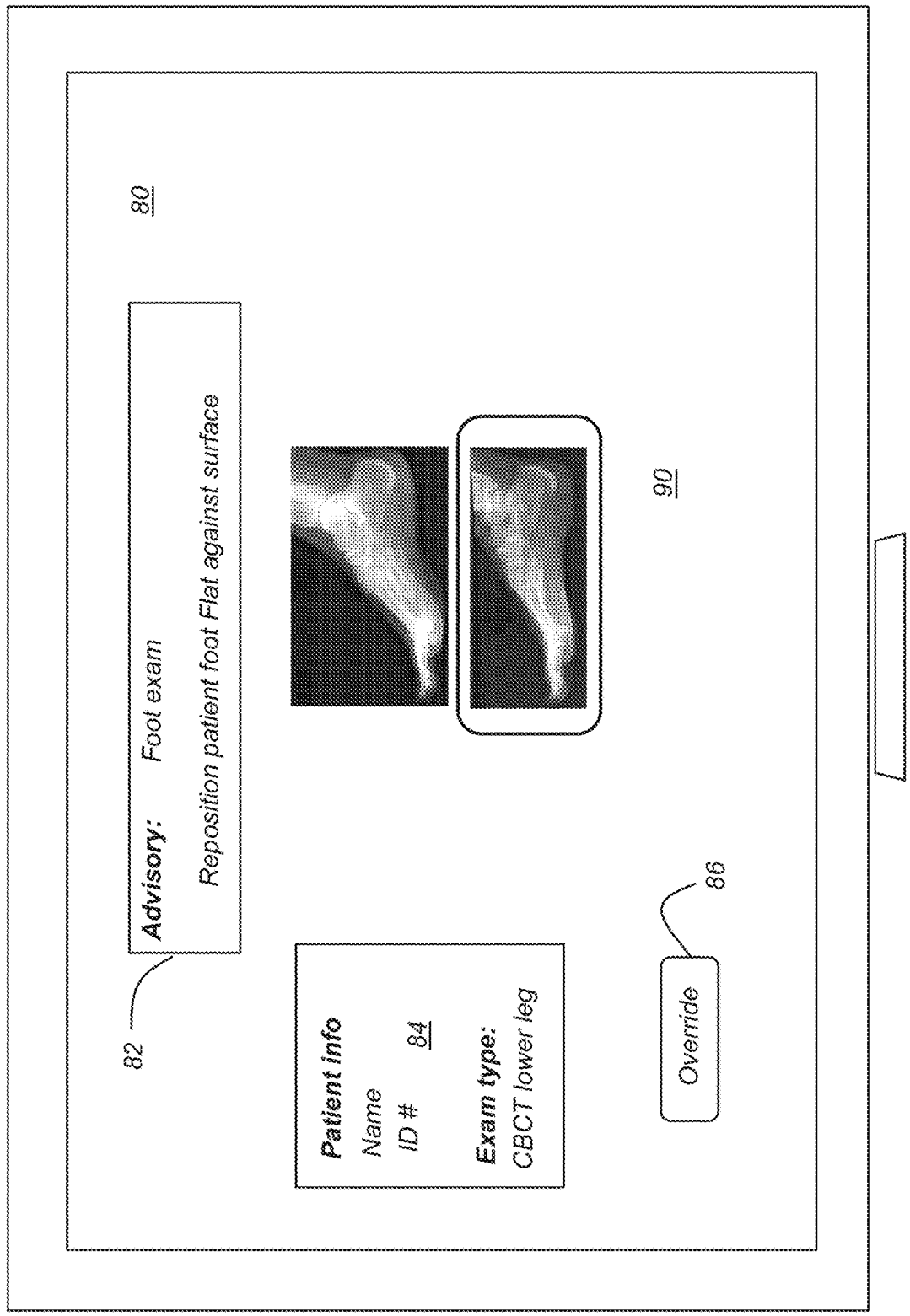

The schematic view of FIG. 7B shows an example report screen 80 with operator selections for patient posture desired for an image. This can allow the technician to adjust for different types of images of the same anatomy. For a foot, for example, operator selections may change positioning of the foot against a support surface of the equipment or may change between load-bearing and non-load-bearing conditions.

Figure 8A:
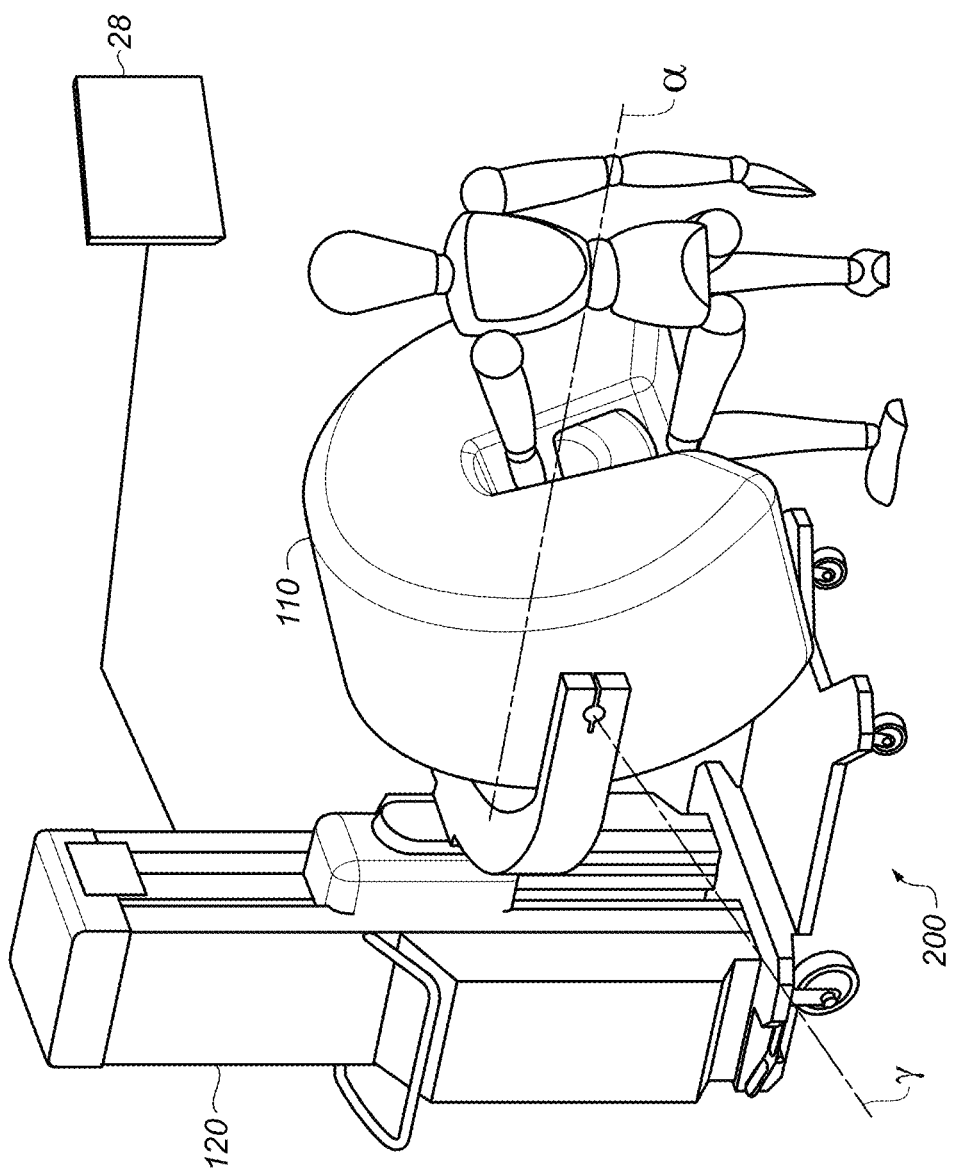
FIGS. 8A and 8B show two different configurations for imaging the arm of a patient, wherein guidance from reflectance imaging for surface contour can be provided directly to the patient.
Figure 8B:
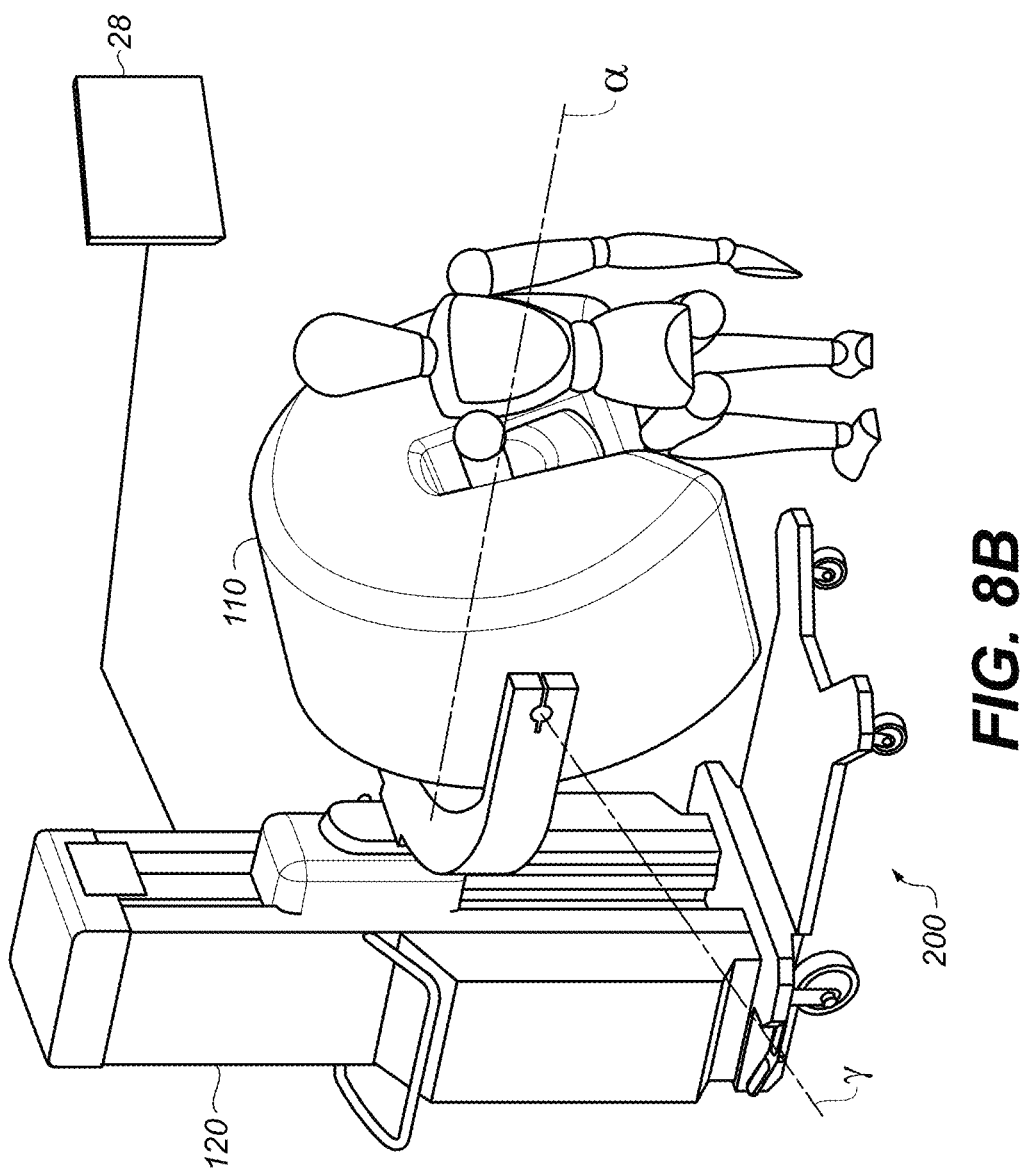

FIGS. 8A and 8B show two different configurations for imaging the arm of a patient, wherein positioning guidance from reflectance imaging for surface contour can be provided directly to the patient. Display 28 of imaging apparatus 200 can provide direct feedback for the patient for assuming the appropriate position as well as for moving from one position to the next. The following references are cited:

Yuan Lin and Ehsan Samei, "A FAST POLY-ENERGETIC FBP ALGORITHM", Physics in Medicine and Biology 59 (2014) pp. 1655-1678;

Yuan Lin and Ehsan Samei, "AN EFFICIENT POLYENERGETIC SART (pSART) RECONSTRUCTION ALGORITHM FOR QUANTITIVE MYCARDIAL CT PERFUSION", Medical Physics, 41 (2) February 2014, pp. 021911-1 to 021911-14;

Qiang M, Chen Y, Zhang K, Li H, Dai H., "Measurement of three-dimensional morphological characteristics of the calcaneus using CT image post-processing", Journal of Foot and Ankle Research. 2014; 7:19. doi:10.1186/1757-1146-7-19.

F. Edward Boas and Dominik Fleischmann. "CT ARTIFACTS: CAUSES AND REDUCTION TECHNIQUES", Imaging Med. (2012) 4 (2), 229-240, pp. 1-19;

US 2008/0095302 (Ruhrnschopf) titled "METHOD FOR HARDENING CORRECTION IN MEDICAL IMAGING";

WO 2016/003957 (Lin) titled "SPECTRAL ESTIMATION AND POLY-ENERGETIC RECONSTRUCTION METHODS AND X-RAY SYSTEMS" published on Jan. 7, 2016.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method comprising:
    displaying, on a display, a first digital image showing a predetermined positioning of an identified radiographic exam;
    acquiring reflectance image content for the identified radiographic exam from patient anatomy disposed within an imaging volume of an imaging apparatus defined between a radiation source and a detector;
    generating a surface contour image from the reflectance image content acquired from the patient anatomy; and
    simultaneously displaying, on a display, the generated surface contour image and the first digital image, thereby allowing a comparison of the images.

2. The method of claim 1 wherein acquiring the reflectance image content comprises acquiring a plurality of structured light images.

3. The method of claim 1 wherein acquiring the reflectance image content comprises acquiring a plurality of ultrasound images.

4. The method of claim 1 wherein generating the surface contour image comprises forming a 3D point cloud or mesh.

5. The method of claim 1 further comprising reporting, on the display, a recommended adjustment to the position of the patient anatomy according to the comparison.

6. The method of claim 5 wherein reporting the recommended adjustment comprises displaying, on the display, a graphic illustrating an outline and an intended outline of the patient anatomy.

7. The method of claim 5 wherein reporting the recommended adjustment comprises providing an audible signal.

8. The method of claim 1 wherein the simultaneously displaying includes displaying one or more measurement dimensions.

9. The method of claim 1 wherein acquiring the reflectance image content is accomplished using a cone beam computed tomography apparatus.

10. The method of claim 1 wherein acquiring the reflectance image content is accomplished using an x-ray imaging apparatus.

11. A method comprising:
projecting a structured light pattern;
using a cone-beam computed tomography (CBCT) imaging apparatus and the projected pattern, acquiring a reflectance image having reflectance image content of the patient's anatomy within the CBCT's imaging volume, the imaging volume being defined between corresponding travel paths of a radiation source and a detector;
generating surface contour image data from the acquired reflectance image content;
comparing the generated surface contour image data with predetermined surface contour image metrics for a pre-defined exam acquired using the CBCT imaging apparatus; and
in response to the comparison, reporting, on a display, a recommended adjustment to the position of the patient anatomy for the pre-defined exam.

12. The method of claim 11 wherein reporting the recommended adjustment comprises displaying, on the display, a graphic illustrating an outline and a recommended outline of the patient's anatomy.

13. A system comprising:
a radiographic imaging apparatus, including:
(a) an x-ray source;
(b) a radiography detector coupled with the x-ray source; and
(c) an imaging volume of interest (VOI) defined as a space between the detector and source for the positioning of a patient;
a contour imaging apparatus adapted to provide a pre-scan of patient anatomy within the VOI;
a computer in signal communication with the radiographic imaging apparatus and the contour imaging apparatus, the computer including a processor to (i) provide a surface contour characterization of the patient anatomy within the VOI acquired by the contour imaging apparatus and (i) compare the characterization with a predetermined surface contour of an identified exam; and
a display, in signal communication with the computer, to display the characterization.

14. The apparatus of claim 13 wherein the contour imaging apparatus comprises a structured light illumination source.

15. The apparatus of claim 13 wherein the contour imaging apparatus uses depth from focus imaging.

16. The apparatus of claim 13 wherein the contour imaging apparatus uses structure from motion processing.

17. The apparatus of claim 13 wherein the contour imaging apparatus uses ultrasound detection.

* * * * *